(12) United States Patent
Neftel et al.

(10) Patent No.: US 6,364,279 B1
(45) Date of Patent: Apr. 2, 2002

(54) PINCH OBTURATING DEVICE FOR A FLEXIBLE TUBE

(75) Inventors: Frédéric Neftel, Lausanne (CH); Bernard Bouvier, Eragny (FR)

(73) Assignee: Debiotech S.A. (CH)

( * ) Notice: Subject to any disclaimer, the term of this patent is extended or adjusted under 35 U.S.C. 154(b) by 0 days.

(21) Appl. No.: 09/679,960

(22) Filed: Oct. 5, 2000

Related U.S. Application Data

(63) Continuation of application No. 09/180,216, filed as application No. PCT/FR97/00771 on Apr. 30, 1997, now abandoned.

(30) Foreign Application Priority Data

May 3, 1996 (FR) ............................................. 96 05543

(51) Int. Cl.⁷ ............................ A61M 39/28; F16K 7/06
(52) U.S. Cl. ................. 251/9; 251/4; 251/98; 604/250
(58) Field of Search ............................ 251/4, 9, 90, 95, 251/98; 604/32, 34, 248, 250

(56) References Cited

U.S. PATENT DOCUMENTS

| | | |
|---|---|---|
| 2,245,774 A | 6/1941 | Gregorek |
| 4,248,401 A | 2/1981 | Mittleman |
| 4,714,463 A | 12/1987 | Archibald et al. |
| 5,026,019 A | 6/1991 | Biekart et al. |
| 5,083,743 A * | 1/1992 | Gordon et al. ............ 251/95 X |
| 5,290,239 A | 3/1994 | Classey et al. |
| 5,337,747 A | 8/1994 | Neftel ....................... 128/635 |
| 5,437,635 A | 8/1995 | Fields et al. |
| 5,437,642 A | 8/1995 | Thill et al. |
| 5,480,386 A | 1/1996 | Brohy et al. ................. 604/131 |
| 5,518,378 A | 5/1996 | Neftel et al. ............. 417/477.2 |
| 5,655,897 A | 8/1997 | Neftel et al. ............. 417/477.2 |
| 5,718,568 A | 2/1998 | Neftel et al. ................ 417/476 |
| 5,741,125 A | 4/1998 | Neftel et al. ............. 417/477.7 |
| 5,759,015 A | 6/1998 | Van Lintel et al. ......... 417/322 |
| 5,764,159 A | 6/1998 | Neftel .................... 340/870.09 |
| 5,782,611 A | 7/1998 | Neftel et al. ................. 417/234 |
| 5,827,262 A | 10/1998 | Neftel et al. ................. 604/414 |
| 5,853,398 A * | 12/1998 | Lal et al. ..................... 604/250 |
| 5,968,014 A | 10/1999 | Neftel et al. ................. 604/151 |
| 6,117,115 A * | 9/2000 | Hill et al. .................... 604/250 |

FOREIGN PATENT DOCUMENTS

| | | |
|---|---|---|
| EP | 405 097 | 1/1991 |
| WO | WO 09514497 | 6/1995 |
| WO | WO 09519195 | 7/1995 |
| WO | WO 09614820 | 5/1996 |
| WO | WO 09621151 | 7/1996 |
| WO | WO 09635472 | 11/1996 |
| WO | WO 09702853 | 1/1997 |
| WO | WO 09715339 | 5/1997 |
| WO | WO 09826818 | 6/1998 |

* cited by examiner

*Primary Examiner*—Kevin Shaver
*Assistant Examiner*—Eric Keasel
(74) *Attorney, Agent, or Firm*—Wolf, Greenfield & Sacks, P.C.

(57) ABSTRACT

The invention relates to a closure device for closing a hose by pinching, and in particular for closing a flexible tube or hose used in the medical field. Essentially, the device comprises a closure piece (62) provided with a circularly arcuate slot (70) which is extended by a circular orifice (76). The closure piece (62) can be rotated about a point O on a circle of radius (R) equal to the radius of the slot (70).

20 Claims, 7 Drawing Sheets

PINCH OBTURATING DEVICE FOR A FLEXIBLE TUBE

This application is a continuation of application Ser. No. 09/180,216, filed Nov. 2, 1998, now abandoned, which is a 371 of PCT/FR97/00771, filed Apr. 30, 1997.

BACKGROUND OF THE INVENTION

1. Field of the Invention

The present invention relates to a device for closing a hose by pinching it.

More precisely, the invention relates to a mechanical device enabling a flexible tube or hose to be closed completely by pinching in order to interrupt the flow of a liquid, the tube or hose being, in particular, of the type used in the field of medicine for administering medication or other similar agents to patients by perfusion.

2. Description of the Related Art

Devices are already known in the medical field enabling such a hose to be closed by longitudinally displacing a piece which includes a rectilinear slot that terminates at one of its ends in a circular recess. When the hose is located in the circular recess, normal liquid flow takes place, whereas when the piece is moved in linear translation, the slot pinches the hose, thereby interrupting the flow of liquid. However, in such systems, the hose is not closed in very reliable manner since there is a risk of the wall of the hose deforming or kinking, thereby enabling a residual flow to be maintained along the hose, and that is unacceptable.

Such a device for closing a hose by pinching is usable in the medical field, in particular with a peristaltic pump for causing a liquid to flow under pressure from a liquid storage bag to a perfusion line. Such peristaltic pumps are of small size and it is therefore advantageous for the closure device itself to be small in size and adapted to the structure of such a peristaltic pump.

Prior art closure devices, in particular those described in U.S. Pat. Nos. 5,437,635 and 5,290,239, not only fail to provide good closure of the flow of liquid along the hose, but in addition they are not adapted to use in association with an ambulatory peristaltic pump of small size.

Peristaltic pumps are well known in this field.

Such peristaltic pumps are described in particular in patent application WO-95/31643 published on Nov. 23, 1995 in the name of the Applicant. Such pump devices are essentially constituted by a pump module proper, or "cassette", which contains presser wheels co-operating with a deformable tubular element that can be removably inserted in a motor unit, the motor unit enabling the presser wheels to be rotated and thus enabling the peristaltic pump to operate. In which case, it will be understood that when the motor stops and the pump proper is extracted from the case of the motor, the pump wheels no longer perform their function of providing local sealing of the tube element, and that liquid can thus flow under gravity through the pump and along the associated tube. In this particular case, it is therefore essential to provide, in association with the peristaltic pump, a mechanical device for closing the tube in order to avoid any accident due to misoperation of the cassette, whether by hospital staff or by the patient.

BRIEF DESCRIPTION OF THE SUMMARY

The present invention provides a device that closes a hose by pinching, particularly but not exclusively a device associated with a peristaltic pump to enable the flow to be interrupted effectively and completely while preferably being compatible with the peristaltic pump.

According to the invention, a device for closing a hose by pinching, where the zone of the hose that is to be closed has an axis XX', the device being characterized in that it comprises:

a moving closure piece having a slot in the form of a circular arc of radius R, said slot having a first end and a second end, said second end being connected to a recess of dimensions that are not less than the dimensions of the right section of the hose, said slot having in the vicinity of its first end a width that is suitable for pinching said hose completely, the second end of the slot having a width that flares to connect with said recess;

means for defining a fixed axis of rotation YY' that is substantially parallel to said axis XX' of the hose;

means for guiding said closure piece in rotation about said axis of rotation in such a manner that said slot moves generally along a circle of radius equal to the radius R, centered on said axis of rotation, and disposed in a plane orthogonal to said axis of rotation; and means for rotating said closure piece between a first position in which the hose passes freely through said recess of the closure piece and a second position in which said hose is pinched in the first end of said slot.

It will be understood that because of the circular displacement of the closure piece which includes a closure slot that is itself circular, effective and complete closure of the hose is obtained by displacement of the closure slot in a circular movement.

Preferably, the device further comprises fixed means for holding said hose substantially stationary in the displacement direction of said closure piece. Also preferably, the device comprises means for locking said closure piece in its second position.

In a preferred embodiment, the device for closing the outlet hose from a peristaltic pump which comprises a housing, a first cylindrical nozzle for connection to an inlet hose, and a second nozzle for connection to said outlet hose, said nozzles having axes that are substantially parallel, is characterized in that it comprises a first assembly mounted in fixed manner on said second nozzle to define said holding means, said locking means, and a portion of said means for providing guidance in rotation, and a second assembly pivotally mounted about said first nozzle to define said arm, said closure piece, a portion of the means for providing guidance in rotation, and the means for displacing said closure piece in rotation.

It will be understood that in this particular application, the embodiment of the closure device is particularly well adapted for use with a peristaltic pump, since the device is reduced to no more than two parts that are very simple, using one of the nozzles of the peristaltic pump as a fixing member for one of the parts of the closure device and the other nozzle of the peristaltic pump as a pivot axis for the moving second aspart of the closure device.

BRIEF DESCRIPTION OF THE DRAWINGS

Other characteristics and advantages of the invention appear better on reading the following description of a preferred embodiment of the invention given by way of non-limiting example. The description refers to the accompanying figures, in which:

FIG. 6b is a section view on line B—B of FIG. 6a;

FIG. 9b is a section view on line B—B of FIG. 9a; and

DETAILED DESCRIPTION

In the description below, there is described an embodiment of the closure device for mounting on the housing of a peristaltic pump. Nevertheless, the invention could be embodied in other ways suitable for closing a hose, in particular in the medical field in order to interrupt mechanically the flow of a liquid along the hose.

Figure 1:
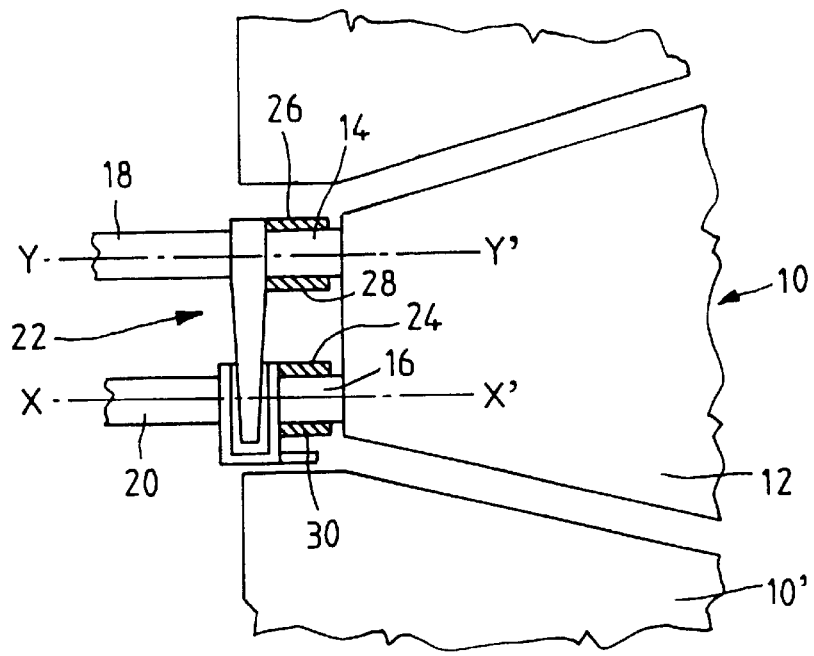
FIG. 1 is a simplified view showing how two parts of the closure device are mounted on the housing of a peristaltic pump.

FIG. 1 shows in simplified manner how the two parts of the closure device are mounted on a peristaltic pump 10. In the figure, the housing 12 of the peristaltic pump is shown diagrammatically together with two nozzles, respectively an inlet nozzle 14 and an outlet nozzle 16 on which the inlet hose 18 and the outlet hose 20 are respectively fixed. Also shown diagrammatically is the case 10' of the pump motor in which the pump or cassette can be engaged in removable manner. In the description below, it is thus the outlet hose 20 which is to be closed mechanically. Each of the nozzles 14 and 16 is cylindrical in shape and the nozzles have respective axes XX' and YY' that are parallel to each other.

As already mentioned, the closure device given overall reference 22 is made up of two parts, firstly a fixed part 24 serving essentially for holding the hose 20 that is to be closed and for guiding the second part 26 of the closure device, which part is essentially constituted by a pivoting piece for closing the hose.

In the preferred embodiment, the part 26 including the closure piece is mounted to pivot about the axis YY' by means of a cylindrical sleeve 28, while the part 24 is mounted in fixed manner on the nozzle 16, likewise by means of a cylindrical sleeve 30. The purpose of FIG. 1 is merely to show how the device is mounted, and it therefore does not show the device in detail.

Figure 5:
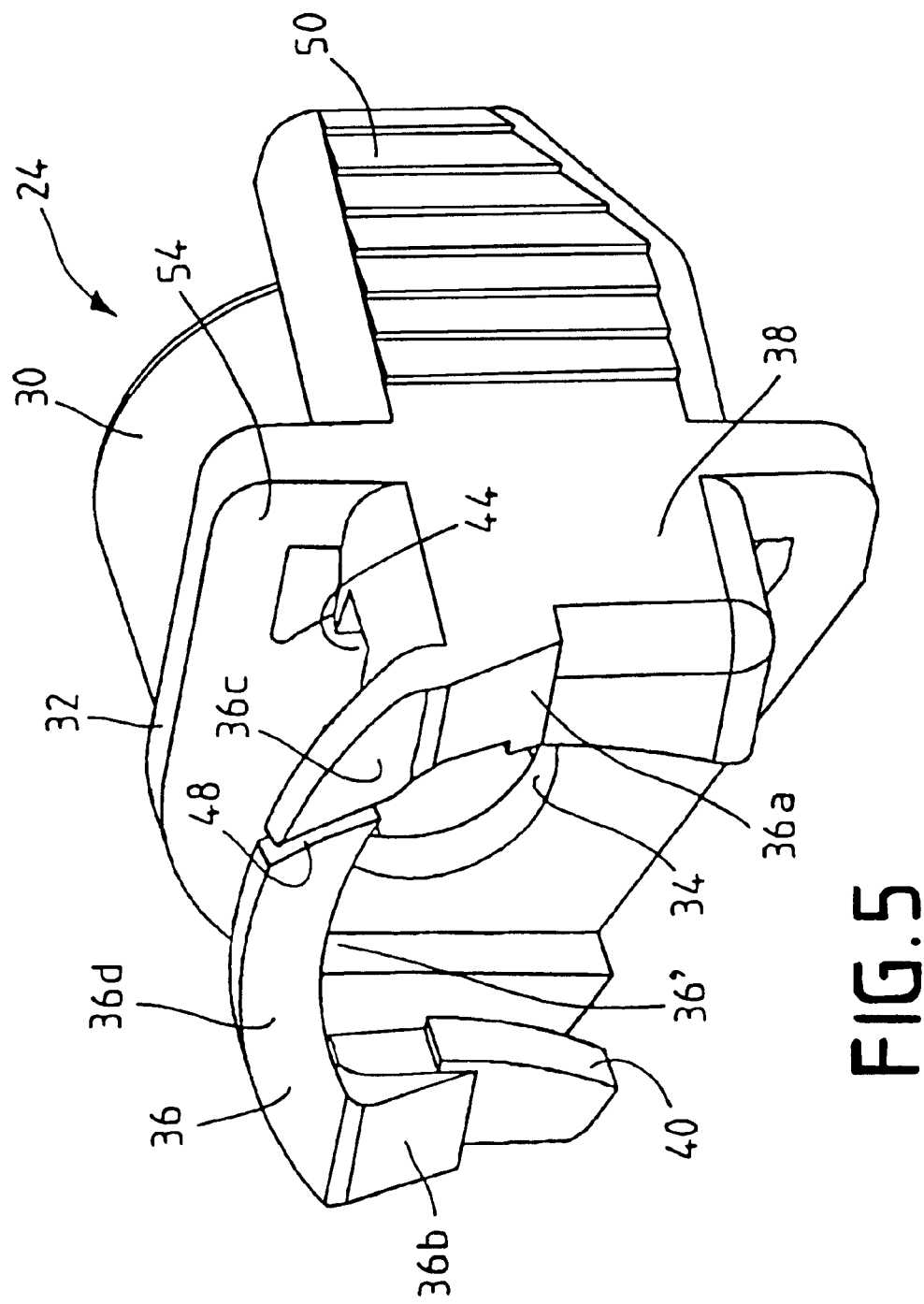
FIG. 5 is a perspective view of the holding position of the closure device of FIG. 2, shown on its own.
Figure 6A:
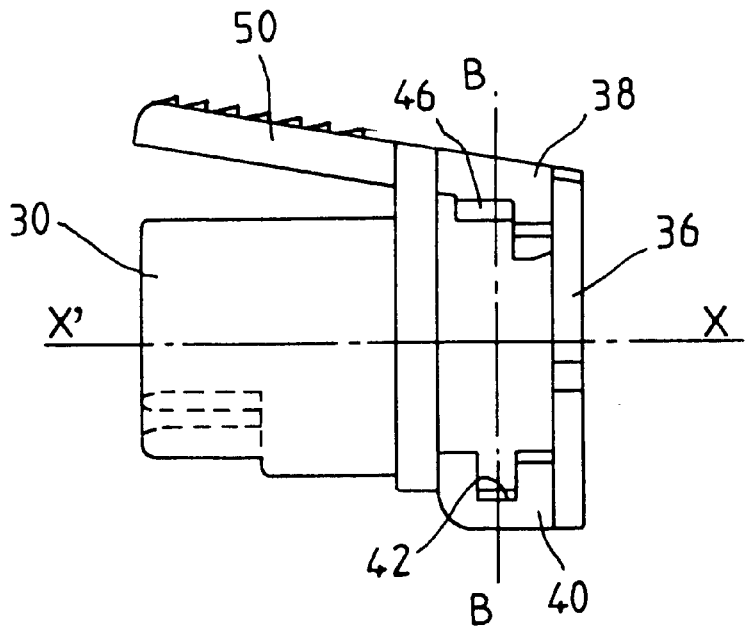
FIG. 6a is a plan view of the portion for holding the closure device of FIG. 2.
Figure 6B:
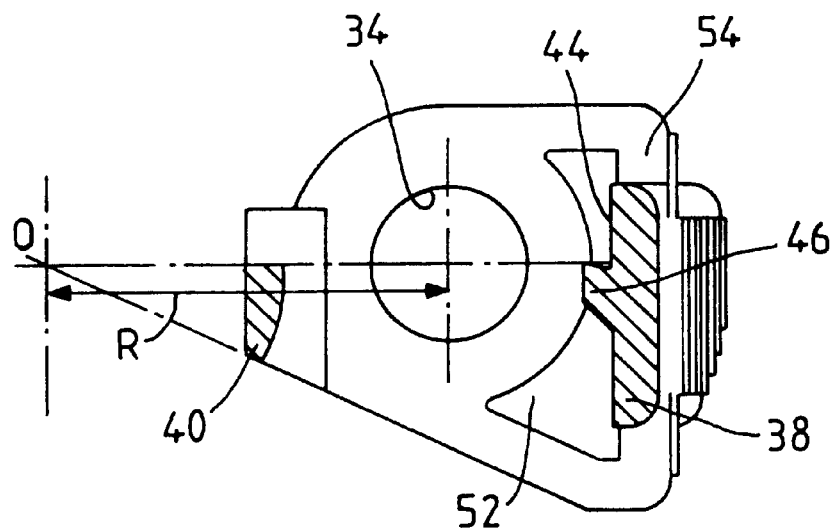
Figure 7:
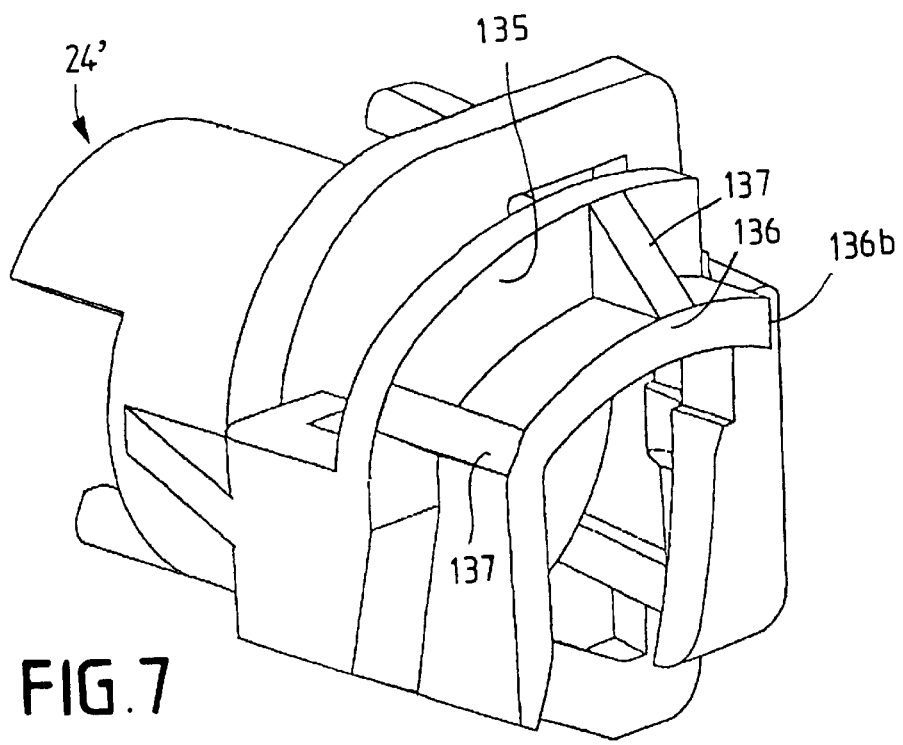
FIGS. 7 and 8 are perspective views of a second embodiment of the holding parts.
Figure 8:
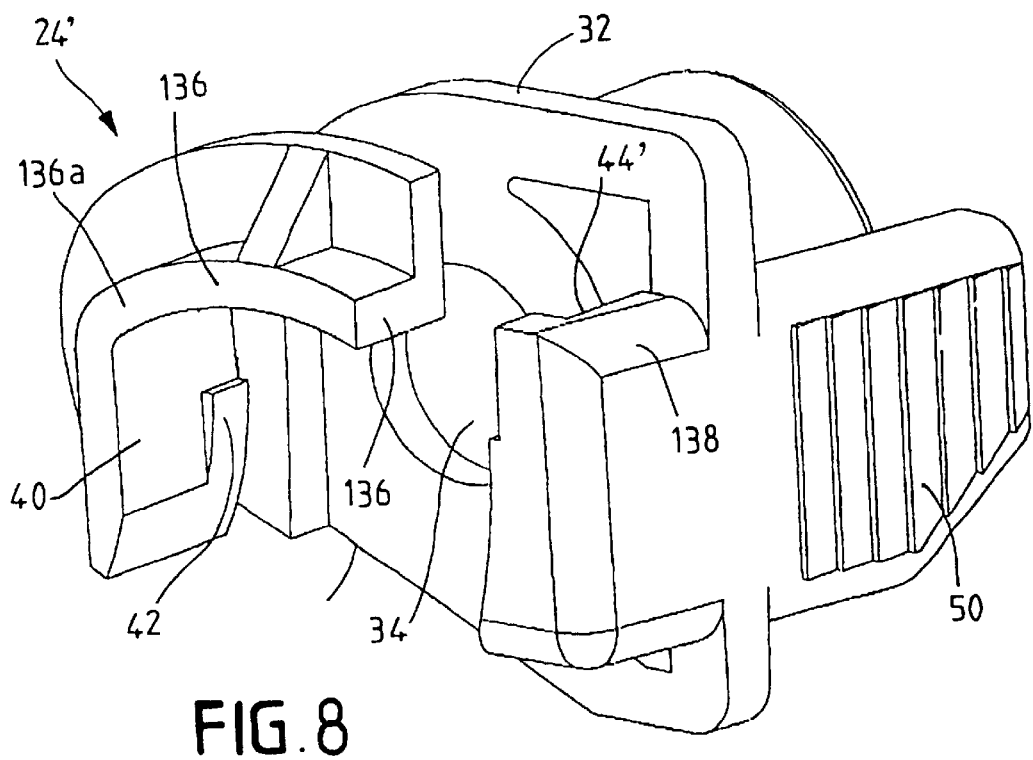
Figure 9A:
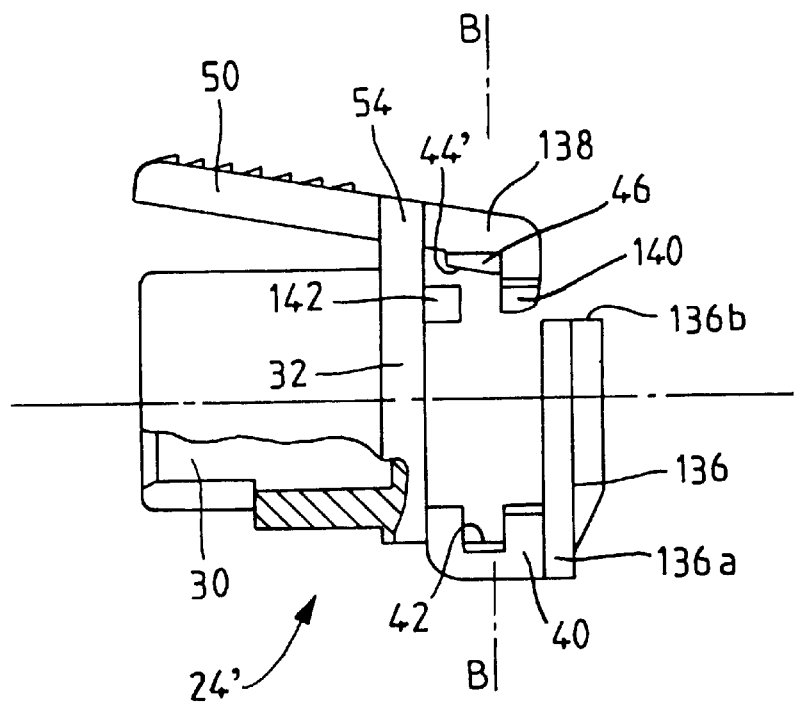
FIG. 9a is a plan view of the second embodiment of the holding part.
Figure 9B:
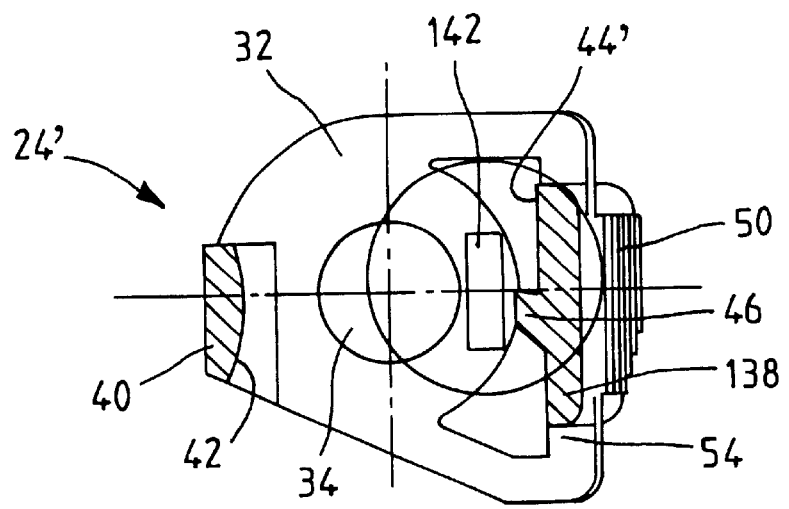

With reference initially to FIGS. 5, 6a and 6b there is described a preferred first embodiment of the holding part 24.

This part is essentially constituted by a plate 32 secured to the fixing sleeve 30 and extending orthogonally to the axis XX'. The plate is provided with a circular orifice 34 of diameter substantially equal to the outside diameter of the hose to be closed. In front of the plate 32 relative to the sleeve 30, there can be seen a member for holding the hose 36, which member is substantially in the form of a circular arc. This member is connected at its two ends 36a and 36b to the two ends of the plate 32 via connection portions 38 and 40. There thus exists an empty space between the plate 32, the holding member 36, and the connection portions 38 and 40 which, as explained below, serves as a passage for the closure piece. As shown in the figures, each connection portion 38 and 40 is provided in its inside face with a respective guide groove 42, 44 likewise in the form of a circular arcs but centered on the axis YY' of the other nozzle of the peristaltic pump. As can be seen better in FIG. 6b, the groove 44 of the connection portion 38 is provided with a stud 46 whose function is explained below. In addition, and as can be seen, the circularly arcuate portion 36 of the holding member is provided with an inclined slot 48 thus defining two portions 36c and 36d of the holding member 36.

As can also be seen in FIGS. 5 and 6a, the connection portion 38 is extended beyond the plate 32 by an actuator tongue 50, said tongue 50 exactly extending the connection portion 38. It can also be seen that the plate 32 is in fact provided with a recess 52, thus defining a vertical portion of the plate 54 on which there are fixed on opposite sides the connection portion. 38 and the tongue 50. It will be understood that because of the recess 52, it is possible, by pressing on the tongue 50, to cause the vertical portion 54 of the plate to pivot by elastic deformation, thereby causing the connection portion 38 to pivot in corresponding manner for reasons that are explained below. It will also be understood that this pivoting of the connection portion 38 is made possible by the presence of the inclined slot 48 formed in the holding member 36.

It should also be specified that the holding member 36 is disposed in such a manner that its bottom face 36' is substantially in contact with the top edge of the hose to be closed.

With reference now to FIGS. 7 through 9b, a second embodiment of the holding part is described, which part is now referenced 24'.

It differs from the holding part 24 in the way in which the holding member 36 is made and the way in which the rib 44 is formed in the connection portion 38.

The new holding member 136 is connected solely by its end 136a to the connection portion 40. Its other end 136b is free. The holding member 136 is thus cantilevered out. Preferably, it has stiffening ribs 135 and 137. It performs exactly the same function as the member 36 by preventing the hose 20 from being raised.

The guide groove 44 of FIG. 5 is replaced by a groove 44' which is defined by a rim 140 on the connection portion 138 and by a rib 142 projecting from the front face of the plate 32 where it faces the rim 140. The stud 46 is to be found on the rib 44'.

In this embodiment, it will be understood that the connection portion 138 is free to pivot about the portion 54 of the plate 32 under the effect of the tongue 50 being actuated since this connection portion is not connected to the holding member 136.

Figure 2:
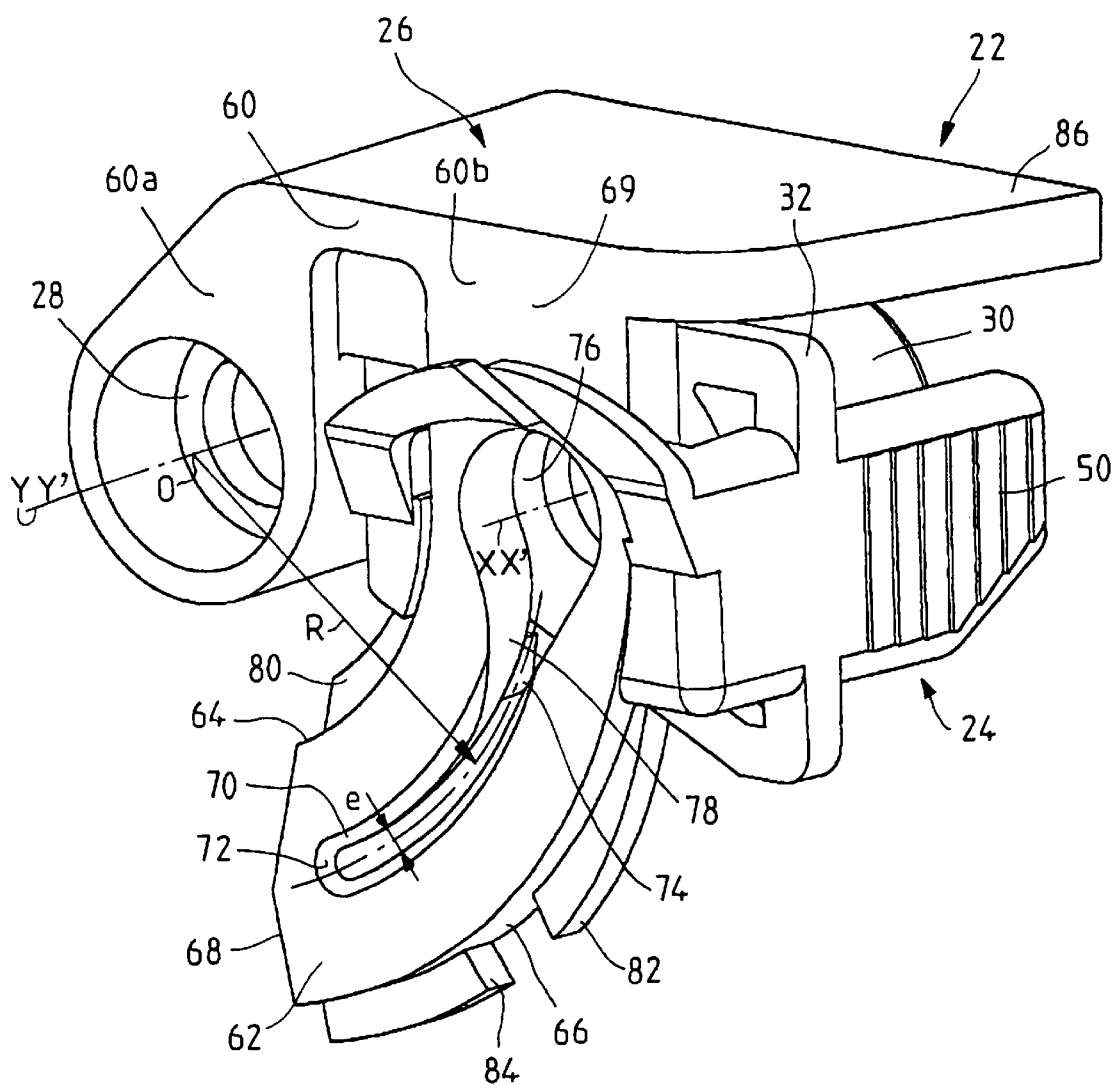
FIG. 2 is a perspective view from the right showing a first embodiment of the closure device in its normal operating position.
Figure 3:
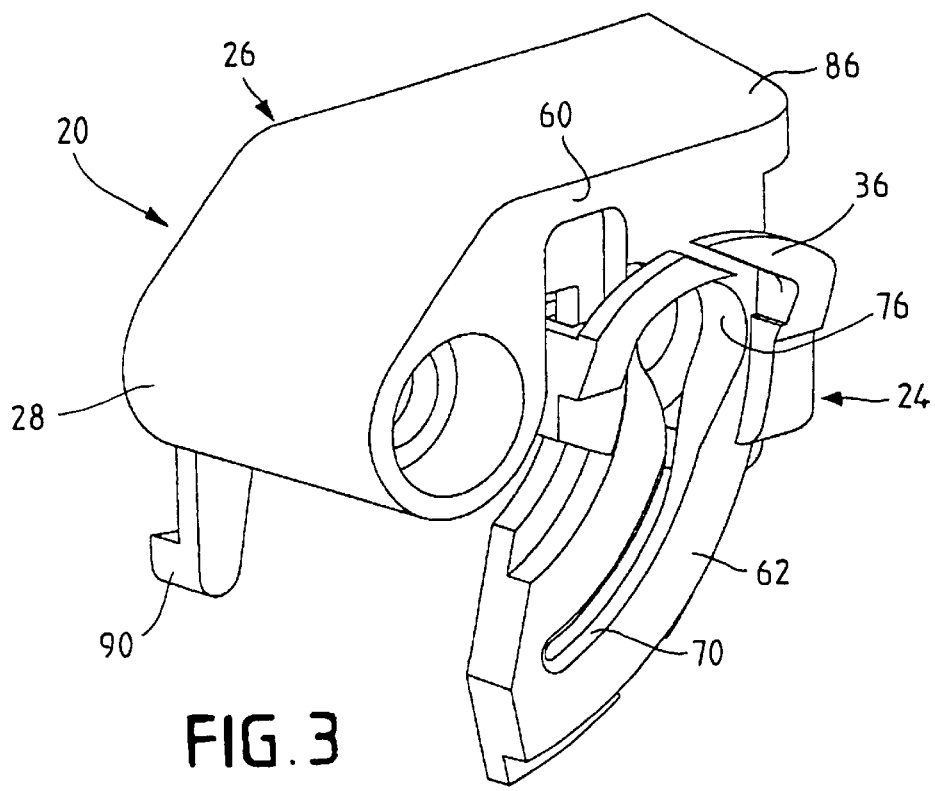
FIG. 3 is a perspective view from the left of the FIG. 2 closure device, the device likewise being in the open position.

With reference more particularly to FIGS. 2 and 3, there follows a description of the moving closure part of the closure device which can be used with both embodiments of the holding part 24 or 24'.

This part 26 is essentially constituted by the sleeve 28 which is pivotally mounted on the nozzle 14. In other words, the closure part 26 is capable of pivoting about the axis YY' which is parallel to the axis XX' of the hose to be closed, and more particularly, this part can pivot about said axis substantially in a plane that is clearly perpendicular to said axis and thus perpendicular to the axis of the hose to be closed. The part 26 is essentially constituted by an arm-constituting portion 60 whose first end 60a is connected to the sleeve 28 and whose second 60b is connected to a closure piece 62. The closure piece 62 is generally in the form of a circular arc defined by an inner circular edge 64 and an outer circular edge 66, the closure piece 62 having a first free end 68 and a second free end 69 connected to the end 60b of the arm 60.

The circular edges 64 and 66 of the closure piece 62 are concentric circular arcs whose commnon center is the point O on the pivot axis YY'.

The circularly arcuate plate constituting the closure piece 62 is provided in its middle portion with a slot 70. This slot has a first end 72 close to the end 68 of the piece 62 and a second end 74. The slot 70 is extended by a recess 76 that is preferably circular in shape having a diameter that is slightly greater than the outside diameter of the hose to be closed. The end 74 of the slot 70 runs tangentially into the zone 78 in the circular recess 76. The running portion of the slot 70 is of a width $e$ which is substantially equal to or preferably slightly less than twice the thickness of the wall of the hose that is to be closed. The middle line of the slot 70 and the center of the recess 76 lie on a circular arc of radius R centered on the axis YY'. The lips of the slot 70 are preferably rounded or the like in a section plane perpendicular to the plane of the piece 62, or are at least of a shape that has no sharp edges so as to avoid any risk of damaging the hose.

FIG. 2 also shows that the edges 64 and 66 of the closure piece 62 are provided with circularly arcuate ribs respectively referenced 80 and 82 which co-operate with the grooves 44 or 44' and 42 formed in the holding portions of the holding part 24. It will thus be understood that when the closure piece 62 pivots about its axis YY', this piece is also guided by co-operation between the ribs 80, 82 and the grooves 42, 44 or 44'. It therefore moves in a plane which is accurately perpendicular to the axis XX' of the tube.

Figure 4:
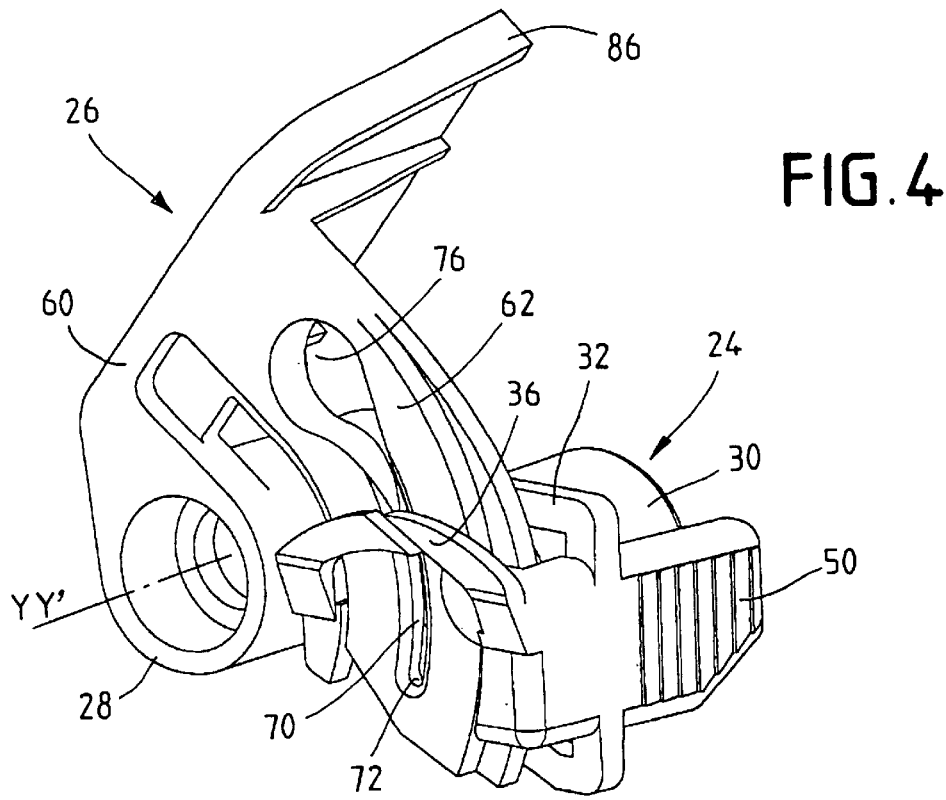
FIG. 4 is a perspective view of the closure device in the closed position.

In FIG. 2, it can be seen that the rib 82 has a notch forming a discontinuity 84 of a length that is sufficient to enable the stud 46 to be engaged therein. The notch 84 is disposed in such a manner that the stud 46 penetrates into the notch 84 when the closure piece 62 is in the position shown in FIG. 4, i.e. in its closure position, and the closure piece is thus locked in its closure position. In addition, it can be seen that the thickness of the rib 82 increases on approaching the end 68 of the piece 62. This makes it possible to ensure that locking is achieved because of the possibility of pivoting the connection portion 38 or 138.

The closure device described above is used as follows:

In normal operation of the peristaltic pump, the closure part 26 is in the position shown in FIGS. 2 and 2, i.e. the outlet hose 20 is free and passes through the orifice 34, the recess 76 of the closure piece, and the holding member 36 or 136. When it is desired to close the hose by means of the device, pressure is applied to the control plate 86 secured to the arm 60. By raising the plate 86, the closure piece is caused to pivot upwards. Since the tube is held in the upward direction by the wall of the orifice 34 and by the holding member 36 or 136, raising the closure piece 62 causes the bottom portion of the tube to engage in the flared zone 78 of the slot 70. This begins to pinch the bottom edge of the tube in the converging zone 78 and this pinching becomes complete as the closure piece is raised until the closure piece reaches its final position, in which position the tube is fully pinched and its walls are slightly compressed so as to obtain total closure of the tube.

Figure 10:
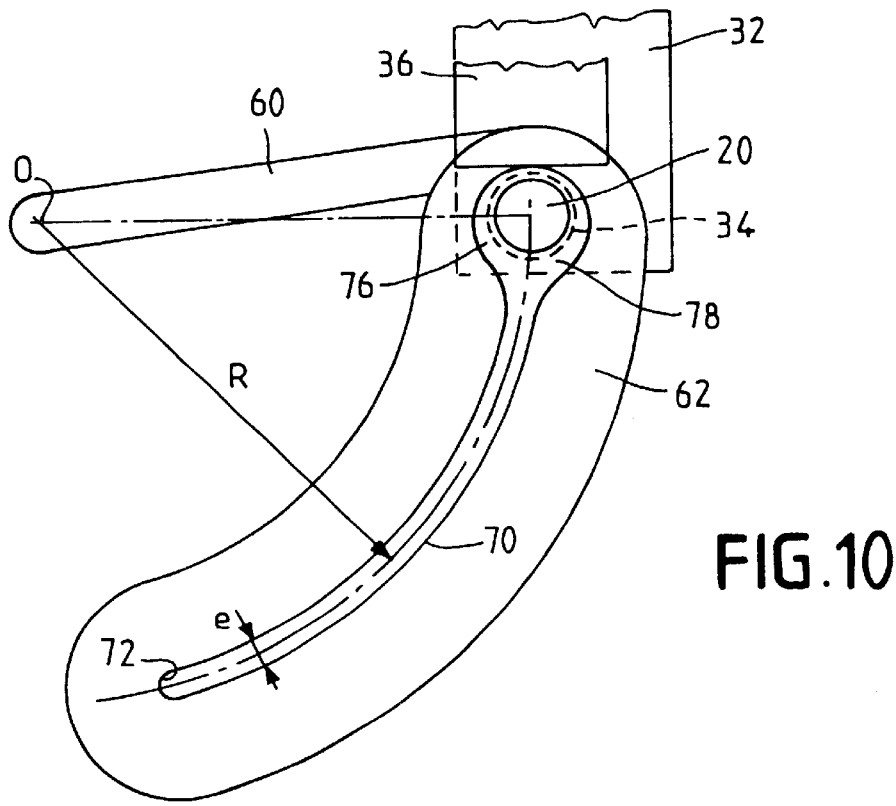
FIG. 10 is a diagram showing the principle on which the closure device operates.

It is important to emphasize that because of the circular displacement of the closure slot combined with the circular shape of said slot and with the tube being held by the portion 24 or 24', the walls of the hose are indeed fully compressed without there being any risk of kinking that could still allow a small amount of liquid flow to take place. FIG. 10 shows this operating principle.

In addition, when the closure piece has been moved to its final position, the locking stud 46 penetrates into the notch 84 of the closure piece, thereby keeping the hose closed. To release the piece 62, it is necessary to act on the tongue 50 to move the stud 46 away, and thus make it possible to lower the piece 62 again.

Preferably, as shown in FIG. 3, the closure part 26 has a hook 90 on the bottom portion of its sleeve 28, with the hook projecting from the sleeve. When the closure device is in its normal operating position, i.e. in the position shown in FIGS. 2 and 3, the hook 90 co-operates with a complementary part (not shown) of the case 10' of the motor associated with the peristaltic pump 10, and it is therefore impossible to extract the cassette of the peristaltic pump 10 while the closure part is in its open position. In contrast, when the closure piece 62 has been moved into the position shown in FIG. 4, i.e. into its closure position, where the piece 62 is locked relative to the part 24 of the closure device, the hook 90 is released so it is possible to remove the cassette 10 freely from the peristaltic pump and out of the case of the motor.

What is claimed is:

1. A closure device, comprising:
   a housing, a first hose, a second hose, a first cylindrical nozzle secured to said housing for connection to said first hose and a second cylindrical nozzle secured to said housing for connection to said second hose, said first and second nozzles extending from said housing in a substantially parallel, side-by-side relationship; and
   a moving closure piece rotatably connected to said housing about said first nozzle, and including a slot in a form of a circular arc extending from a first slot end to a recess of a dimension that is not less than an outside diameter of said second hose, wherein said first slot end has a reduced width for completely pinching said second hose and preventing fluid flow, and wherein said recess forms a second slot end.

2. The closure device according to claim 1 further comprising an arm having a first end pivotally mounted to said housing about an axis of rotation and having a second end connected to said moving closure piece.

3. The closure device according to claim 2, wherein said nozzles have axes that are substantially parallel, and wherein said axis of rotation of said arm is substantially parallel to said nozzle axes.

4. The closure device according to claim 3 wherein said closure piece includes an arc-shaped plate defined by an inner circular edge and an outer circular edge and having a first end associated with said first slot end and a second end associated with said recess, said arc-shaped plate being connected to said arm.

5. The closure device according to claim 4 further including a first cylindrical sleeve co-operatively arranged with said first cylindrical nozzle for holding said first hose in a removable manner, and a second cylindrical sleeve co-operatively arranged with said second cylindrical nozzle for holding nd hose in a removable manner.

6. A closure device comprising:
   a housing, a first hose, a second hose, a first cylindrical nozzle secured to said housing for connection to said first hose and a second cylindrical nozzle secured to said housing for connection to said second hose, said first and second nozzles having nozzle axes that are substantially parallel to one another;

a moving closure piece rotatably connected to said housing and including a slot in a form of a circular arc extending from a first slot end to a recess of a dimension that is not less than an outside diameter of said second hose, wherein said first slot end has a reduced width for completely pinching said second hose and preventing fluid flow, said recess forming a second slot end, said closure piece including an arc-shaped plate defined by an inner circular edge and an outer circular edge and having a first end associated with said first slot end and a second end associated with said recess;

an arm having a first end pivotally mounted to said housing about an axis of rotation substantially parallel to said nozzle axes and a second end connected to said moving closure piece on said arc-shaped plate;

a first cylindrical sleeve cooperatively arranged with said first cylindrical nozzle to hold said first hose in a removable manner;

a second cylindrical sleeve cooperatively arranged with said second cylindrical nozzle to hold said second hose in a removable manner; and a holding member having a first end and a second end, wherein at least one of said ends of said holding member is attached to said second cylindrical sleeve, said holding member being constructed to prevent said second hose from moving while said closure piece is being moved from its first position to its second position.

7. A closure device for an outlet hose, comprising:

a housing, an inlet hose, a first cylindrical nozzle secured to said housing for connection to said inlet hose and a second nozzle secured to said housing for connection to said outlet hose, said nozzles having axes that are substantially parallel, said nozzles extending in substantially the same direction from the housing in a substantially side-by-side relationship;

a moving closure piece rotatably mounted about said first nozzle and having a rotation axis substantially parallel to said nozzle axes, said closure piece including a slot in a form of a circular arc substantially centered on said axis of said first nozzle, said slot having a first end and a second end, said second end being connected to a recess of a dimension that is not less than an outside diameter of the outlet hose, said slot having in the vicinity of its first end a width that is suitable for completely pinching said outlet hose and preventing fluid flow, the second end of the slot having a width that flares to connect with said recess;

means for guiding said closure piece in rotation about said rotation axis, said guiding means being connected to said first nozzle and comprising an arm having a first end which is rotatably mounted about said first nozzle and a second end which is connected to said closure piece; and means for rotating said closure piece between a first position in which said outlet hose passes freely through said recess of the closure piece and a second position in which said outlet hose is pinched in the first end of said slot.

8. The closure device according to claim 7, wherein said inlet hose provides an inlet to a pump and said outlet hose provides an outlet to said pump.

9. The closure device according to claim 7, wherein said closure piece includes a plate in a form of a circular arc defined by an inner circular edge and an outer circular edge and having a first end corresponding to the first end of the slot and a second end corresponding to said recess, and wherein said second end of said arm of said guiding means is connected to one end of said plate.

10. The closure device according to claim 9, wherein said guiding means comprise a second plate secured to said second nozzle and provided with an orifice of a diameter slightly greater than an outside diameter of said outlet hose, said second plate being disposed in a plane orthogonal to an axis of said outlet hose.

11. The closure device according to claim 7, further comprising means for locking said closure piece in its second position.

12. The closure device according to claim 11, further including a first cylindrical sleeve and a second cylindrical sleeve mounted on said first and second nozzles respectively, the second sleeve being mounted to pivot on the second nozzle.

13. The closure device according to claim 12 wherein said second pivotally mounted sleeve has a locking member suitable for co-operating with a complementary member when the closure piece is not in its second position.

14. A closure device for an outlet hose comprising:

a housing, an inlet hose, a first cylindrical nozzle secured to said housing for connection to said inlet hose and a second nozzle secured to said housing for connection to said outlet hose, said nozzles having axes that are substantially parallel;

a moving closure piece rotatably mounted about said first nozzle and having a rotation axis substantially parallel to said nozzle axes, said closure piece including a slot in a form of a circular arc substantially centered on said axis of said first nozzle, said slot having a first end and a second end, said second end being connected to a recess of a dimension that is not less than an outside diameter of the outlet hose, said slot having in the vicinity of its first end a width that is suitable for completely pinching said outlet hose and preventing fluid flow, the second end of the slot having a width that flares to connect with said recess, said closure piece further including a plate in a form of a circular arc defined by an inner circular edge and an outer circular edge and having a first end corresponding to the first end of said slot, a second end corresponding to said recess and an arm having a first end rotatably mounted about said first nozzle and a second end connected to one end of said plate;

means for guiding said closure piece in rotation about said rotation axis, said guiding means being connected to said first nozzle, said guiding means comprising a second plate secured to said second nozzle and having an orifice of a diameter slightly greater than an outside diameter of said outlet hose, said second plate being disposed in a plane generally orthogonal to an axis of said outlet hose;

means for rotating said closure piece between a first position in which the outlet hose passes freely through said recess of the closure piece and a second position in which the outlet hose is pinched in the first end of said slot; and a holding member offset axially relative to said second plate and being secured to said second plate in such a manner that said closure piece can move between said second plate and said holding member, said holding member being substantially in contact with said outlet hose and being constructed to prevent said outlet hose from moving while said closure piece is being moved from its first position to its second position.

15. The closure device according to claim 14, wherein said holding member has a first end and a second end and is secured to the second plate via said first end, while said second end is not attached to said housing.

16. The closure device according to claim 15, wherein the holding member is in the form of a circularly arcuate portion having said second end free and having said first end connected to said second plate via a first connection portion and wherein said holding member comprises a second connection portion secured to said second plate and projecting from said second plate.

17. The closure device according to claim 14, wherein said holding member is in the form of an arc of a circle having a first end connected to said second plate by a first connection portion and having a second end connected to said second plate by a second connection portion.

18. The closure device according to claim 17, wherein said holding member has a slot between its first and second ends.

19. The closure device according to claim 17, wherein the closure piece includes inner and outer edges provided with respective ribs suitable for co-operating with groove-forming means of circularly arcuate shape formed in each of the connection portions of the holding member.

20. The closure device according to claim 19 further comprising locking means comprising a stud formed in the groove-forming means of the second connection portion, said stud being suitable for co-operating with a notch formed in the associated rib of said closure piece, said second connection portion being extended by an unlocking tongue, the link between the second connection portion and firstly the tongue and secondly an edge of the second plate constituting a pivot axis enabling the second connection portion to pivot relative to the second plate, action on said tongue enabling the second connection portion to pivot in a temporary manner to allow said stud to escape from said notch.

* * * * *